United States Patent
Kaiser et al.

[11] Patent Number: 6,090,772
[45] Date of Patent: Jul. 18, 2000

[54] TRICLOSAN SKIN WASH WITH ENHANCED EFFICACY

[75] Inventors: Nancy E. Kaiser, Pontoon Beach, Ill.; Denise K. Pretzer, Chesterfield, Mo.

[73] Assignee: Steris Inc, Temecula, Calif.

[21] Appl. No.: 09/360,250

[22] Filed: Jul. 23, 1999

Related U.S. Application Data

[63] Continuation-in-part of application No. 08/890,521, Jul. 9, 1997, Pat. No. 5,955,408.
[60] Provisional application No. 60/021,453, Jul. 10, 1996.

[51] Int. Cl.$^7$ .................. C11D 1/12; C11D 3/44; C11D 3/48
[52] U.S. Cl. .......... 510/388; 510/130; 510/131; 510/138; 510/382; 510/383; 510/393; 510/429; 510/432; 510/477; 510/480; 510/342; 510/386; 510/471
[58] Field of Search ................ 510/130, 131, 510/138, 382, 383, 388, 393, 429, 432, 477, 480, 342, 386, 471

[56] References Cited

U.S. PATENT DOCUMENTS

| | | | |
|---|---|---|---|
| 4,975,218 | 12/1990 | Rosser | 252/117 |
| 5,006,529 | 4/1991 | Resch | 514/721 |
| 5,057,311 | 10/1991 | Kamegai et al. | 424/70 |
| 5,364,031 | 11/1994 | Taniguchi et al. | 239/330 |
| 5,415,810 | 5/1995 | Lee et al. | 252/545 |
| 5,417,875 | 5/1995 | Nozaki | 252/106 |
| 5,635,469 | 6/1997 | Fowler et al. | 510/406 |
| 5,681,802 | 10/1997 | Fujiwara et al. | 510/130 |
| 5,716,626 | 2/1998 | Sakurai et al. | 424/401 |

FOREIGN PATENT DOCUMENTS

| | | |
|---|---|---|
| 1408885 | 10/1975 | United Kingdom . |
| WO 93/07250 | 4/1993 | WIPO . |
| WO 95/09605 | 4/1995 | WIPO . |
| WO 95/24179 | 9/1995 | WIPO . |
| WO 95/32705 | 12/1995 | WIPO . |
| WO 96/06152 | 2/1996 | WIPO . |

*Primary Examiner*—Yogendra Gupta
*Assistant Examiner*—Charles Boyer
*Attorney, Agent, or Firm*—Fay, Sharpe, Fagan, Minnich & McKee, LLP

[57] ABSTRACT

A disinfectant hand wash includes Triclosan and a reduced amount of surfactants in order to reduce skin irritation while maintaining improved activity against Gram negative and Gram positive organisms, including *Serratia marcescens*. The hand wash includes an effective amount of Triclosan, preferably 0.2–3.0% and a non-aqueous solvent. Hexylene glycol, or a mixture of hexylene glycol and isopropanol as the non-aqueous solvent provide improved efficacy in killing skin-born microbes. The hand wash further includes less than about 10% surfactant, preferably less than 5%. The hand wash further includes a chelating agent, a thickener, a buffering agent, and water.

22 Claims, 8 Drawing Sheets

TRICLOSAN SKIN WASH WITH ENHANCED EFFICACY

This application is a Continuation-In-Part which claims the benefit of U.S. application Ser. No. 08/890,521, filed Jul. 9, 1997, now U.S. Pat. No. 5,955,408 which claims the benefit of U.S. Provisional Application No. 60/021,453, filed Jul. 10, 1996.

BACKGROUND OF THE INVENTION

The present invention relates to the antimicrobial arts. It finds particular application in conjunction with the removal of microorganisms from the skin of health care personnel and will be described with particular reference thereto. It should be appreciated, however, that the invention is also applicable outside the medical area, such as a hand wash for workers in the food preparation industry, a wash for consumer and home health care, or other areas where skin disinfection is advisable.

The chemical control of bacteria and viruses is assuming increasing importance in the hospital and medical environment. The situation has been exacerbated by the failure of many bacteria to respond to conventional antibiotics. Accordingly, the need for effective control of bacterial and viral organisms is assuming greatly increased significance. In the case of hand and skin disinfection, a biocidal agent is desired which kills the widest possible range of microorganisms in the least possible time without toxicity, irritation or other hazards. It is further desirable for the biocidal agent to retard reinfection of the skin for a significant duration after application.

Hand wash formulations have been developed using Triclosan as a biocidal agent. Triclosan has broad spectrum activity against a wide variety of microorganisms. However, Triclosan is not readily soluble in aqueous systems. To solubilize the Triclosan, it is conventional to use a surfactant, usually in an amount of 15–30% of the formulation. At such levels, the surfactant tends to cause skin irritation. This is particularly troublesome to health care workers, who are employing skin washes several times a day.

The present invention provides for a new and improved skin wash formulation and method of use, which overcomes the above-referenced problems, and others.

SUMMARY OF THE INVENTION

In accordance with the present invention, an improved health care personnel skin wash is provided. The skin wash includes:

(a) about 0.2 to about 3.0% Triclosan;
(b) about 1.0 to about 30.0% of a non-aqueous solvent which includes hexylene glycol;
(c) less than about 10.0% surfactant;
(d) about 0.0 to about 1.0% chelating agent;
(e) about 0.0 to about 3.0% thickener;
(f) about 0.0 to about 5.0% buffering agent; and
(g) water.

In accordance with another aspect of the present invention a method of disinfecting skin is provided. The method includes applying to the skin an effective amount of the above composition and maintaining contact between the composition and the skin for sufficient time to kill substantially all microorganisms present on the surface.

In accordance with another aspect of the present invention a skin wash composition is provided. The composition includes (a) about 0.2 to about 3.0% Triclosan;
(b) about 1.0 to about 30.0% of a non-aqueous solvent which includes a glycol and a lower alcohol selected from the group consisting of isopropanol, ethanol, and n-propanol;
(c) less than about 8.0% surfactant;
(d) about 0.0 to about 1.0% chelating agent;
(e) about 0.0 to about 3.0% thickener;
(f) about 0.0 to about 5.0% buffering agent; and
(g) water.

In accordance with another aspect of the present invention, a skin wash composition is provided. The skin wash includes:

(a) 0.2–1.5% Triclosan;
(b) 2.0–8.0% surfactant;
(c) 4–15% hexylene glycol;
(d) 3–10% lower alcohol;
(e) a buffer which buffers pH to 4.5–6.0%; and
(f) a thickener which adjusts viscosity to 500–2500 cps.

One advantage of the invention resides in improved activity against Gram negative organisms. In particular, the formulations have improved activity over other formulations against *Serratia marcescens*, a Gram negative organism which is one of the most difficult to kill.

Another advantage of the invention resides in improved activity against Gram positive organisms.

Yet another advantage of the invention is an improved kill rate of microorganisms by the handwash as compared with skin wash formulations at higher surfactant concentrations.

A further advantage of the invention is that triclosan in the skin wash formulation is solubilized at low surfactant levels.

A yet further advantage of the invention is that reinfection of skin surfaces after treatment with the skin wash is reduced.

Other advantages of the invention include efficacy at low surfactant concentrations, a reduction in the skin irritation typically associated with Triclosan hand wash formulations, and a superior cleaning effect to hand washes comprising primarily alcohols.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

A skin wash is provided which contains an antibacterial agent, including Triclosan in an effective amount, a surfactant, and a non-aqueous solvent. Triclosan is present in the hand and skin wash formulations in an amount from about 0.1 to about 3.0%. Preferably, the amount of Triclosan is from about 0.3 to about 1.5%.

Unfortunately, Triclosan has very poor solubility in water and generally requires formulation additives to solubilize it. The most common additives used to solubilize Triclosan are surfactants which increase skin irritation. The present formulations minimize this problem by using non-aqueous solvents and lower levels of surfactants to solubilize the Triclosan.

The non-aqueous solvents (or "co-solvents") used in the formulations are generally present in an amount from about 1.0 to about 30%. Preferably, these solvents are present in an amount from about 3.0 to about 20.0%. Examples of suitable non-aqueous solvents include glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations of these. Glycols are particularly preferred co-solvents. Especially preferred are the combinations of a glycol, particularly hexylene glycol, and one or more lower alcohols, particularly isopropanol, n-propanol, and ethanol.

Hexylene glycol has been found to have especially good characteristics as a co-solvent. Although not fully understood, it appears that the hexylene glycol portion of the co-solvent may solubilize Triclosan by a different mechanism than the surfactant, leaving the Triclosan more effective as a result. Other glycols also show these properties, though generally are less effective than hexylene glycol.

Combining the hexylene glycol with another co-solvent, particularly a lower alcohol, such as isopropanol, has a synergistic effect on the kill rate. Results of tests show a generally higher kill rate with a combination of hexylene glycol with isopropanol, for example, than with either of the two solvents alone or of the individual results added together. The higher kill rates of glycol/alcohol combinations in the skin wash is particularly apparent with Gram negative organisms, although differences (i.e., as compared with hexylene glycol or alcohol alone in the skin wash) are also apparent with Gram positive organisms. Preferred compositions include from about 3–20% hexylene glycol and from about 3–15% lower alcohol, preferably isopropanol. Particularly preferred is a combination of about 4–15% hexylene glycol and about 3–10% isopropanol.

In prior art compositions, surfactants used to solubilize the Triclosan are generally present in amounts of from about 15–30% active surfactant by weight. The surfactants used in the present formulations are generally present in lower amounts, for instance from about 0.5 to about 20.0%, more preferably in an amount from about 1% to about 10%, and most preferably from about 2–8% of the composition. Although good microorganism kill rates are achieved at below about 2% surfactant, it is generally preferred to provide around 2% surfactant, or above, to provide other properties of the skin wash, such as foaming characteristics.

It has been found, unexpectedly, by the present inventors that the microorganism kill rate of the composition is improved when surfactant levels are below about 10%. That is, higher reductions in the number of microorganisms present are achieved, or the time to reduce the microorganism count to at or below an acceptable level is reduced. Additionally, the lower surfactant levels provide compositions which are less irritating to the skin. The low surfactant levels also reduce the tendency for reinfection of the skin surface after treatment with the skin wash. The composition is not washed off the skin as readily as compositions with higher surfactant levels, leaving the active ingredients on the skin and thus available to prevent subsequent reinfection for longer periods of time.

The preferred level of surfactant varies to some degree with the class of surfactant employed. In general, however, all of the surfactants tested showed increasing kill rates as the concentration of surfactant dropped below 10%, with the highest log reductions in microorganism counts occurring at around 3% surfactant, or below. Log reduction is the difference between the log of the original number of organisms present and the log of the number remaining.

The preferred level of surfactant is also dependent on the concentration of non-aqueous solvent and triclosan in the formulation. Specifically, as the concentration of hexylene glycol increases or as the Triclosan concentration increases, higher levels of surfactant can be accommodated in the formulation without a severe effect on the ability of the triclosan to kill microorganisms. Thus, when the Triclosan concentration is above about 1.5%, surfactant levels of about 5–10% can be used and still provide a good kill rate. When the level of triclosan is about 1.5% or less, a particularly preferred concentration of surfactant is about 2–5%. Similarly, at hexylene glycol concentrations of about 15% and above, surfactant levels of up to about 5–10% can be accommodated while maintaining good microorganism kill. Even lower concentrations of hexylene glycol (about 10–15%) maintain good kill rates at the higher surfactant levels (5–10%) when in combination with a lower alcohol, such as isopropanol.

At low Triclosan levels, less cosolvent (non aqueous solvent) is needed to help solubilize the Triclosan than at higher concentrations. For example, at 0.2% Triclosan, a 4% hexylene glycol concentration is sufficient to provide an effective composition, while at 1% Triclosan, a higher concentration of around 18% total cosolvent provides an effective composition when the surfactant level is low (around 3.5%). Preferably, the ratio of cosolvent to Triclosan is from about 5:1 to about 20:1.

As can thus be seen, the preferred concentration of surfactant is dependent on a number of factors, including the concentration of hexylene glycol and other cosolvents, the level of triclosan, and, at the lower end of the range, on chosen surfactant characteristics, such as foaming. The concentration of hexylene glycol and other co-solvents in the skin wash are thus preferably adjusted, within the range, dependent on the desired concentrations of triclosan and surfactant.

Typical examples of surfactants which are useful in the formulations of the invention include nonionic and anionic surfactants such as polyoxyethylene sorbitan fatty acid esters, polyoxyethylene stearates, polyvinyl alcohol, poloxamers, octoxynols, salts of sarcosinates, sulfosuccinates, sulfonates, isethionates, sulfates, amine oxides, taurates, and combinations of these. Amphoteric surfactants, such as imidazolines and their derivatives, particularly amphodiacetates, aminopropionates, alkylaminopropionates and betaines and sultaines, may also be employed alone or in combination with other surfactants.

Suitable sulfates are alkyl ether sulfates of the general formula $R\text{-}(OCH_2CH_2)_n OSO_3\text{—}M^+$, wherein R ranges from $C_8\text{–}C_{20}$ alkyl and preferably from $C_{12}\text{–}C_{15}$ alkyl, n is an integer from 1 to 40, preferably from 2–9, and optimally about 3, and $M^+$ is a sodium, potassium, ammonium, or triethanolammonium cation. Examples of such sulfates include sodium laureth sulfate, obtainable as Standopol ES-3 from Henkel Corp.; TEA laureth sulfate, obtainable as Empicol ET B from Albright & Wilson; sodium laureth-12 sulfate, obtainable as Standopol 125-E from Henkel; sodium trideceth sulfate, obtainable as Cedepal TD-407 from Stepan; ammonium laureth sulfate, obtainable as Standopol EA-2 from Henkel; and mixtures thereof.

Other suitable sulfates include alkyl sulfates, such as ammonium lauryl sulfate, obtainable as Stepanol AM, from Stepan.

Suitable imidazolines include amphodiacetates, such as disodium cocoamphodiacetate obtainable under the trade name Mackam 2C from McIntyre. Other mono and diacetates may also be used.

Suitable betaines and sultaines which may be employed include alkyl betaines of the general formula $RN^+(CH_3)_2 CH_2CO_2\text{—}M^+$, amidopropyl betaines of the formula $RCONHCH_2CH_2CH_2(CH_3)_2CH_2CO_2\text{—}M^+$, and amidopropyl sultaines of the formula $RCONHCH_2CH_2N^+(CH_3)_2 CH_2SO_3\text{—}M^+$, wherein R ranges from $C_8\text{–}C_{20}$ alkyl and preferably from $C_{12}\text{–}C_{15}$ alkyl, and $M^+$ is a water soluble cation, such as sodium, potassium, ammonium, or triethanolammonium cation. Examples of such betaines and sultaines include cocamidopropyl betaine, available as Tego-Betain C from Goldschmidt; cocamidopropyl hydroxysultaine, obtainable as Lonzaine CS from Lonza; coco-betaine, obtainable as Lonzaine 12C from Lonza; myristamidopropylbetaine, obtainable as Schercotaine MAB from Scher; oleyl betaine, obtainable as Velvetex OLB-50 from Henkel; lauramidopropyl betaine (a salt of fatty quaternaryamines), obtainable as Mackam LMB from McIntyre; and mixtures thereof.

Suitable isethionates are those having the general formula $RCOOCH_2CH_2SO_3M$, wherein R is alkyl or alkenyl of from about $C_{10}\text{–}C_{30}$ and M is a water soluble cation, such as sodium, potassium, ammonium, or triethanolammonium. Examples of isethionates include alkoyl isethionates, such as ammonium cocoyl isethionate, sodium cocoyl isethionate; sodium lauroyl isethionate, sodium steroyl isethionate, and mixtures thereof. Ammonium cocoyl isethionate, obtainable as Jordapon ACI-30 from BASF, is a particularly preferred anionic surfactant.

Suitable sulfosuccinates include monoalkyl sulfosuccinates, amido MEA sulfosuccinates, and dimethicone copolyol sulfosuccinates. Examples include disodium lauryl sulfosuccinate obtainable as Emcol 4400–1 from Witco; disodium cocamido MEA sulfosuccinate obtainable as Emcol 5315 from Witco; disodium myristamido MEA sulfosuccinate, obtainable as Emcol 4100M from Witco; Disodium Oleamido MEA sulfosuccinate obtainable as Schercopol OMS-Na from Scher; and ammonium dimethicone copolyol sulfosuccinate, obtainable as Mackanate DC-60A from McIntyre.

Sarcosinates useful in the present invention are of the general formula $RCON(CH_3)CH_2CO_2\text{—}M^+$, wherein R is alkyl from about $C_8\text{–}C_{20}$, preferably $C_{12}\text{–}C_{15}$, and M is a water soluble cation, such as sodium, potassium, ammonium, or triethanolammonium. Examples include ammonium lauroyl sarcosinate obtainable as Hamposyl AL-30 from Hampshire; sodium lauroyl sarcosinate obtainable as Hamposyl L-30 from Hampshire; and TEA cocoyl sarcosinate obtainable as Hamposyl TL-40 from Hampshire.

Chelating agents are used in an amount from 0.0 to about 1.0%. It is particularly preferred that the amount be from about 0.01 to about 0.5%. Typical examples of the kind of chelating agents which are useful in the present formulation include EDTA acid or salts thereof, citric acid or salts thereof, glucuronic acid or salts thereof, pyrophosphate salts, chelating surfactants such as phosphate esters and lauroyl ethylenediaminetriacetic acid, and mixtures of these. The chelating agents serve to improve the effectiveness of the formulation toward Gram negative bacteria.

The polymer/viscosity-inducing agent, or thickener, is present in an amount from 0.0 to about 3.0%, and preferably in an amount from about 0.5 to about 2.0%. Typical examples of these agents include PEG esters, hydroxypropyl methylcellulose, hydroxypropyl cellulose, hydroxyethyl cellulose, carbomer, naturally occurring gums, such as guar, guar derivatives, alginate, and alginate derivatives, and mixtures of these.

The buffering agents are present in an amount from 0.0 to about 5.0%, and preferably in an amount from about 0.1 to about 1.0%. These agents are typically acids or salts used to maintain pH in the range of about 3.0 to about 8.0, and preferably from about 4.5 to about 6.0. Examples include acetic acid/acetate salts, citric acid/citrate salts, glycolic acid/glycolate salts, phosphoric acid/phosphate salts, and mixtures of any of these. The most preferred formulations include citric acid/citrate salts.

Finally, water is used to make up the remainder of the composition.

To prepare the hand wash, the components are mixed together in the proportions described. In order to solubilize the Triclosan completely, it is preferably first mixed in the non-aqueous solvent(s) and/or surfactant(s) before the water is added. The other components are then added when convenient. When the components are mixed together in the proportions described, the viscosity of the composition formed is from about 20 to 10,000 cps. Preferably, the viscosity of the composition formed is from about 500 to 2500 cps.

As noted above, the present formulations have improved activity against Gram negative and Gram positive organisms. The activity against Gram negative organisms is most dramatic with the inclusion of low levels of isopropanol or n-propanol. Such activity is completely unexpected since low levels of isopropanol alone do not show this level of activity. The activity against Gram positive organisms is particularly evident when hexylene glycol is used as a solvent. Accordingly, combinations of isopropanol and hexylene glycol or n-propanol and hexylene glycol are preferred.

The present formulations are applied to the skin surface to be treated in a conventional manner, as one would apply any hand wash or soap. Preferably, the hand wash is dispensed from a bottle or other dispenser and worked into the hands for sufficient time to remove soil and kill microorganisms present on the skin. Water is used to assist in the formation of a lather. To remove the hand wash, it is rinsed off with water.

EXAMPLES

Example 1

Efficacy of an Example Skin Wash Formulation against a Variety of Microorganisms Samples of a Triclosan formulation were inoculated with strains of microorganisms expected to be found on skin surfaces as transients or residents and the effectiveness of the formulation determined in terms of the log reduction in the number of microorganisms.

The following Triclosan hand wash formulation was prepared:

| Material | % by Weight of Active Ingredient |
|---|---|
| Ammonium Hydroxide | 0.0870 |
| Triclosan | 1.0000 |
| Hexylene Glycol | 10.0000 |
| Hydroxypropyl Methylcellulose (Brand - Methocel K15MS) | 0.9500 |
| Ammonium Cocoyl Isethionate (Brand - Jordapon ACI-30) | 4.5000 |
| Diammonium Dimethicone Copolyol Sulfosuccinate (Brand - Mackanate DC-60A) | 0.9000 |
| Ammonium Lauroyl Sarcosinate (Brand - Hamposyl AL-30) | 0.4500 |
| EDTA Acid (Brand - Hampene Acid) | 0.1500 |
| Deionized Water | Q.S. |

The total surfactant concentration in this hand wash formulation was 5.85% by weight.

Preparation of Inoculum

The organisms tested were chosen to represent a broad spectrum of standards and clinical isolates. Table 1 lists the organisms tested and their sources.

For Candida strains, 48 hours prior to testing, Yeast Maltose (YM) agar slants were inoculated with 0.1 mL of stock culture and incubated for 48 hours at 30° C. For other strains that were tested, 24 hours prior to testing, Brain Heart Infusion (BHI) agar slants were inoculated with 0.1 mL of stock culture and incubated at 30° C. for 24 hours. After incubation, the day of testing, cultures were removed from the incubator. Cultures were then resuspended with 10 mL of sterile 0.85% saline solution, yielding a suspension containing approximately $10^9$ organisms.

Time Kill Procedure 10 mL samples of the Triclosan formula were inoculated with 0.1 mL of the approximate $10^9$ microorganism suspension and mixed.

At scheduled intervals, a 1.0 mL portion of the inoculated samples was removed and placed into a neutralizing dilution blank. The neutralizers used were Letheen broth containing 5% heat-inactivated fetal bovine serum for Triclosan. Serial dilutions were performed and plated to the fifth dilution. Counts were compared with an inoculated control to quantify the log reduction of organisms due to the activity of the formulation. Log reduction is the difference between the log of the original number of organisms present and the log of the number remaining, thus an increase in log reduction over time indicates that an increasing number of organisms are destroyed.

The results are shown in Table 1. The data demonstrate that the Triclosan-containing formulation exhibits activity against a broad spectrum of organisms. A range of activity is observed with the greatest rate and extent of kill seen for Gram positive organisms known to reside on skin and to be transferred via hands in the hospital setting.

TABLE 1

TIME KILL RESULTS FOR 1% TRICLOSAN HAND WASH FORMULATION
Sources of Strains
ATCC - American Type Culture Collection
SLU - St. Louis University Hospital, St. Louis, MO.
CH - Children's Hospital, St. Louis, MO.

| | | Log Reduction Time (min) | | | |
|---|---|---|---|---|---|
| Organism | Isolate | 0.25 | 0.50 | 1.00 | 2.00 |
| Gram Positive Organisms | ATCC 6538 | 7.76 | 7.76 | 7.76 | 7.76 |
| Staphylococcus aureus | ATCC 33591 | 0.38 | 0.48 | 0.47 | 0.8 |
| | ATCC 33591(2) | 0.40 | 0.60 | 0.67 | 1.1 |
| | ATCC 33592 | 7.69 | 7.69 | 7.69 | 7.69 |
| | ATCC 33593 | 7.91 | 7.91 | 7.91 | 7. |
| Methicillin-Resistant | SLU 253 | 3.73 | 7.68 | 7.68 | 7. |
| Staphylococcus aureus | CH 6 | 7.77 | 7.77 | 7.77 | 7 |
| | CH 12 | 3.42 | 7.95 | 7.95 | 7 |
| | CH 14 | 2.44 | 3.17 | 7.61 | |
| | CH 23 | 7.60 | 7.60 | 7.60 | |
| Staphylococcus epidermidis | ATCC 12228 | 1.22 | 2.52 | 7.42 | |
| | ATCC 35983 | 0.52 | 0.85 | 2.46 | |
| Staphylococcus epidermidis | CH 600 | 1.74 | 3.28 | 4.37 | |
| | CH 601 | 2.17 | 6.07 | 6.07 | |
| Streptococcus pyogenes | ATCC 8058 | 6.83 | 6.83 | 6.83 | |
| | ATCC 19615 | 6.43 | 6.43 | 6.43 | |
| | ATCC 21059 | 6.27 | 6.27 | 6.27 | |
| | CH 39 | 6.58 | 6.58 | 6.58 | |
| | BMS BMY 597 | 6.59 | 6.59 | 6.59 | |
| | BMS BMY 600 | 6.49 | 6.49 | 6.49 | |
| Enterococcus faecalis | ATCC 27959 | 6.64 | 6.64 | 6.64 | |
| | ATCC 29212 | 6.93 | 6.93 | 6.93 | |
| | ATCC 29302 | 7.01 | 7.01 | 7.01 | |
| | ATCC 33186 | 7.17 | 7.17 | 7.17 | |
| Vancomycin-Resistant | A | 1.19 | 2.47 | 1.24 | 6.35 |
| Enterococcus faecium | E | 1.51 | 2.58 | 3.51 | 4.58 |
| | G | 3.85 | 6.67 | 6.67 | 6.67 |
| | G(2) | 2.57 | 3.44 | 4.38 | 6.49 |
| | H | 4.24 | 6.29 | 6.29 | 6.29 |
| Gram Negative Organisms | ATCC 26 | 0.31 | 0.76 | 1.32 | 2.93 |
| | ATCC 8739 | 0.35 | 0.37 | 0.86 | 2.53 |
| Escherichia coli | ATCC 11229 | -0.57 | -0.43 | 0.54 | 0.27 |
| | ATCC 15221 | 0.04 | 0.14 | 1.19 | 4.21 |
| Escherichia coli | CH 400 | 0.10 | 0.27 | 0.70 | 2.96 |
| | CH 401 | 0.38 | 0.36 | 0.75 | 2.54 |
| | CH 402 | 0.26 | 0.07 | 0.30 | 0.79 |
| Klebsiella pneumoniae | ATCC 8044 | 0.38 | 0.72 | 1.49 | 2.68 |
| | ATCC 13883 | 0.45 | 0.40 | 1.07 | 1.4 |
| | ATCC 27736 | 0.05 | 0.01 | 0.24 | 0.4 |
| | ATCC 33452 | 0.49 | 0.60 | 1.06 | 1. |
| | CH 500 | 0.05 | 0.19 | 0.15 | 0. |
| | CH 501 | -0.15 | -0.12 | -0.04 | 0. |
| | CH 502 | 0.26 | 0.15 | 0.22 | 0 |

TABLE 1-continued

TIME KILL RESULTS FOR 1% TRICLOSAN HAND WASH FORMULATION
Sources of Strains
ATCC - American Type Culture Collection
SLU - St. Louis University Hospital, St. Louis, MO.
CH - Children's Hospital, St. Louis, MO.

| Organism | Isolate | Log Reduction Time (min) | | | |
|---|---|---|---|---|---|
| | | 0.25 | 0.50 | 1.00 | 2.00 |
| Pseudomonas aeruginosa | ATCC 9027 | 7.32 | 7.32 | 7.32 | 7 |
| | ATCC 14502 | 2.88 | 3.88 | 7.36 | |
| | ATCC 15442 | 4.98 | 8.02 | 8.02 | |
| | ATCC 27853 | 6.29 | 4.41 | 7.76 | |
| | CH 300 | 5.58 | 8.11 | 8.11 | |
| | CH 301 | 4.69 | 7.94 | 7.94 | |
| | CH 302 | 7.79 | 7.79 | 7.79 | |
| | CH 303 | 3.47 | 7.93 | 7.93 | |
| Serratia marcescens | ATCC 8195 | 0.56 | 0.60 | 0.79 | |
| | ATCC 14756 | 0.18 | 0.29 | 0.37 | |
| | CH 200 | 0.18 | 0.28 | 0.49 | |
| | CH 201 | 0.22 | −0.08 | 0.25 | 0.65 |
| Yeast | ATCC 10259 | 0.37 | 0.27 | 0.62 | 0.81 |
| Candida albicans | ATCC 18804 | −0.61 | −0.65 | −0.15 | −0.04 |
| | ATCC 24433 | −0.24 | 0.02 | 0.23 | 0.28 |
| | ATCC 38483 | 0.13 | 0.07 | 0.74 | 0.95 |
| | CH 100 | 0.32 | 0.03 | 0.11 | 0.23 |
| | CH 101 | 0.23 | −0.07 | 0.02 | 0.13 |
| | CH 102 | 0.30 | 0.10 | 0.24 | 0.46 |
| | CH 103 | 0.16 | 0.16 | 0.21 | 0.76 |

Example 2

Efficacy of a Second Skin Wash Formulation against a Variety of Microorganisms A Triclosan hand wash composition was prepared according to the formula listed below and the procedures described in Example 1 repeated to determine the effectiveness of the formulation for destruction of the microorganisms listed in table 2. The neutralizers used in this example were Letheen broth containing either 5% heat-inactivated fetal bovine serum or 6% of a 3.5% asolecithin and 25% Tween 80 solution. The results shown in table 2 indicate that the modified formula was effective at destroying all organisms tested, even the Gram negative organisms such as *Serratia marcescens* that proved somewhat resistant to the formula used in Example 1. Of those organisms that were not completely destroyed within two minutes of exposure to the modified Triclosan formulation, all were destroyed within a total of 3–5 minutes exposure.

Modified Triclosan Hand Wash Formulation

| Ingredient | % by Weight |
|---|---|
| Triclosan | 1.0 |
| Ammonium Cocoyl Isethionate | 3.6 |
| Hexylene Glycol | 13.0 |
| Isopropanol (isopropyl alcohol) | 5.0 |
| Hydroxypropyl methyl cellulose | 0.85 |
| Diammonium EDTA | 0.4 |
| Citric Acid | 0.05 q.s. to pH 5.0–5.5 |
| Deionized water | Q.S. |

TABLE 2

TIME KILL RESULTS FOR MODIFIED 1% TRICLOSAN HAND WASH FORMULATION
Sources of Strains
ATCC - American Type Culture Collection
SLU - St. Louis University Hospital, St. Louis, MO.
CH - Children's Hospital, St. Louis, MO.
Baseline counts are indicated under "isolate".

| Organism | Isolate | 0.25 | 0.50 | 1.00 | 2.00 |
|---|---|---|---|---|---|
| Gram Positive Organisms | ATCC 6538 (7.8) | 7.80 | 7.80 | 7.78 | 7.8 |
| Staphylococcus aureus | ATCC 33591 (7.25) | 7.25 | 7.25 | 7.25 | 7.2 |
| | ATCC 33592 (7.0) | 7.00 | 7.00 | 7.00 | 7.0 |
| | ATCC 33593 (7.68) | 7.91 | 7.91 | 7.91 | 7. |
| Methicillin-Resistant Staphylococcus aureus | SLU 253 (6.98) | 6.98 | 6.98 | 76.98 | 6. |
| | CH 6 (7.64) | 7.64 | 7.64 | 7.64 | 7. |
| | CH 12 (7.95) | 7.95 | 7.95 | 7.95 | 7 |
| | CH 14 (7.49) | 7.49 | 7.49 | 7.49 | 7 |
| Staphylococcus epidermidis | ATCC 12228 (6.66) | 6.66 | 6.66 | 6.66 | 6 |
| | ATCC 35983 (7.16) | 7.16 | 7.16 | 7.16 | |
| Staphylococcus epidermidis | CH 600 (7.13) | 7.13 | 7.13 | 7.13 | |
| | CH 601 (7.69) | 7.69 | 7.69 | 7.69 | |
| Enterococcus faecalis | ATCC 27959 (7.08) | 7.08 | 7.08 | 7.08 | |
| | ATCC 29212 (7.42) | 7.42 | 7.42 | 7.42 | |
| | ATCC 29302 (7.58) | 7.58 | 7.58 | 7.58 | |
| | ATCC 33186 (7.55) | 7.55 | 7.55 | 7.55 | |
| Vancomycin-Resistant Enterococcus faecium | A (6.64) | 4.80 | 6.64 | 6.64 | |
| | E (6.60) | 6.60 | 6.60 | 6.60 | 6.60 |
| | G (6.58) | 6.58 | 6.58 | 6.58 | 6.58 |
| | H (6.69) | 6.69 | 6.69 | 6.69 | 6.69 |
| Gram Negative Organisms | ATCC 26 (7.71) | 0.92 | 2.02 | 5.40 | 7.71 |
| Escherichia coli | ATCC 8739 (7.98) | 1.17 | 3.14 | 7.98 | 7.98 |
| | ATCC 11229 (7.61) | 0.66 | 1.88 | 6.13 | 7.61 |
| | ATCC 15221 (7.74) | 0.83 | 0.93 | 2.77 | 7.74 |
| Escherichia coli | CH 400 (7.78) | 0.42 | 1.07 | 3.93 | 7.78 |
| | CH 401 (7.75) | 0.67 | 1.27 | 3.29 | 7.75 |
| | CH 402 (7.84) | 0.75 | 0.82 | 1.57 | 4.94 |
| Pseudomonas aeruginosa | ATCC 9027 (7.67) | 7.67 | 7.67 | 7.67 | 7.67 |
| | ATCC 14502 (7.49) | 7.49 | 7.49 | 7.49 | 7.49 |
| | ATCC 15442 (7.92) | 7.92 | 7.92 | 7.92 | 7.92 |
| | ATCC 27853 (7.7) | 7.70 | 7.70 | 7.70 | 7.70 |
| | CH 300 (7.89) | 7.89 | 7.89 | 7.89 | 7.89 |
| | CH 301 (7.77) | 7.77 | 7.77 | 7.77 | 7.77 |
| | CH 302 (7.62) | 7.62 | 7.62 | 7.62 | 7.62 |
| | CH 303 (7.42) | 7.42 | 7.42 | 7.42 | 7.42 |
| Serratia marcescens | ATCC 8195 (7.68) | 0.27 | 1.76 | 4.39 | 7.68 |
| | ATCC 14756 (8.01) | 0.21 | 0.44 | 1.30 | 3.45 |
| | CH 200 (7.67) | 0.07 | 0.22 | 0.98 | 1.5 |
| | CH 201 (7.80) | 0.42 | 0.56 | 1.65 | 5.7 |

Example 3

Effect of Selection of Diol or Glycol on Microorganism Kill

Figure 1:
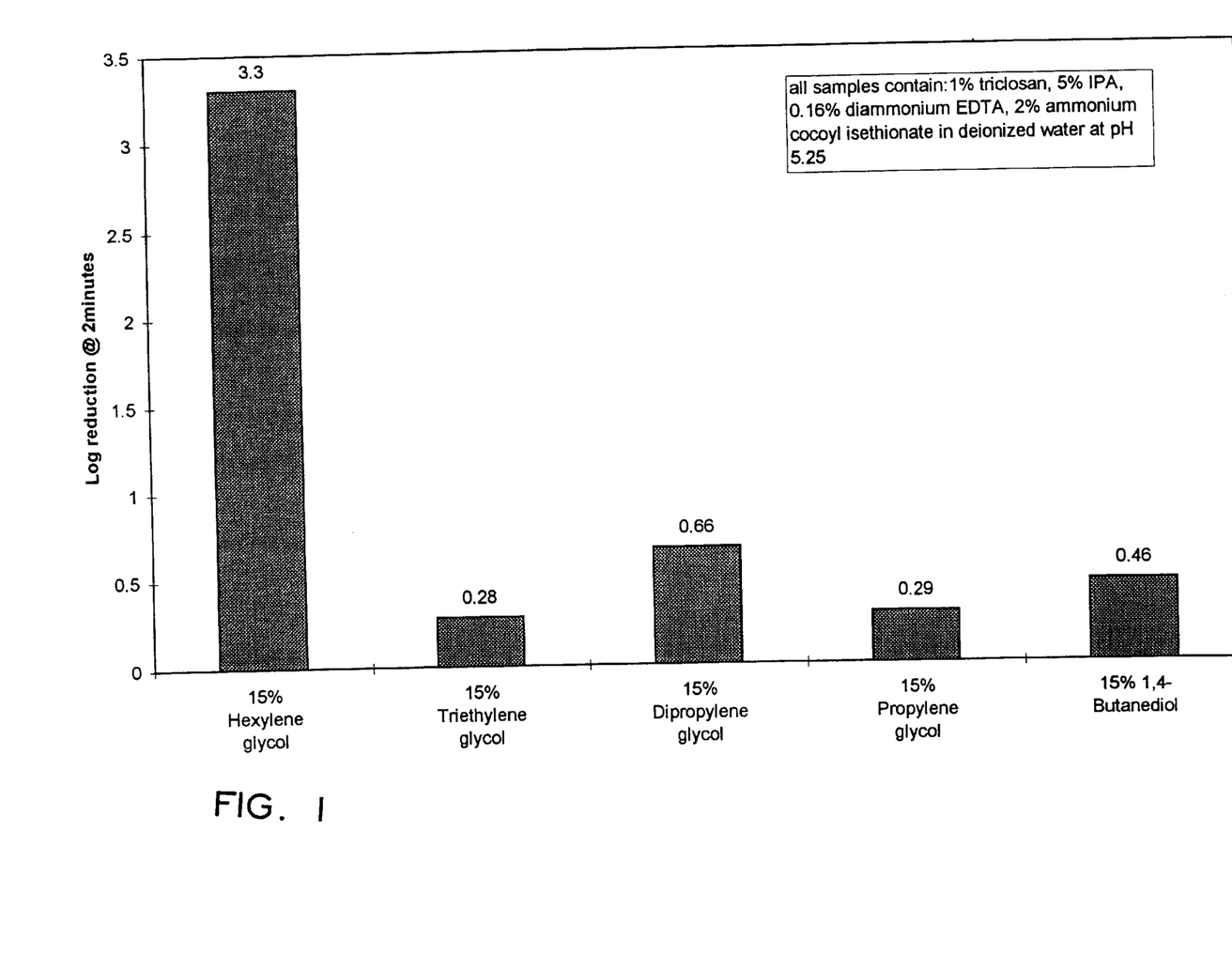
FIG. 1 is a plot of Log reduction of *Serratia marcescens* ATCC 14756 organisms after 2 minutes exposure to 1% triclosan formulations containing 2% ammonium cocoyl isethionate and 15% of a one of a group of glycol and diol co-solvents.

Triclosan skin wash formulations were prepared according to the method described in Example 1. The skin wash formulations contained 1% Triclosan, 2% ammonium cocoyl isethionate, 5% isopropanol, and 0.16% diammonium EDTA in deionized water at pH 5.25. The hand washes also included 15% of a glycol or diol selected from the group consisting of hexylene glycol, triethylene glycol, dipropylene glycol, propylene glycol, and 1,4-butanediol. Log reductions in a population of Serratia marcescens ATCC 14756 were measured after 2 minutes seconds exposure to the handwash, in each case. FIG. 1 shows that the kill rate (log reduction) for the hexylene glycol containing skin wash, was substantially higher than for the other glycols or diols tested. At 15% hexylene glycol, a log reduction of 3.3 was obtained, compared with 0.66 for dipropylene glycol and 0.46 for butanediol.

Example 4

Effect of Hexylene Glycol Concentration on Microorganism Kill

Figure 2:
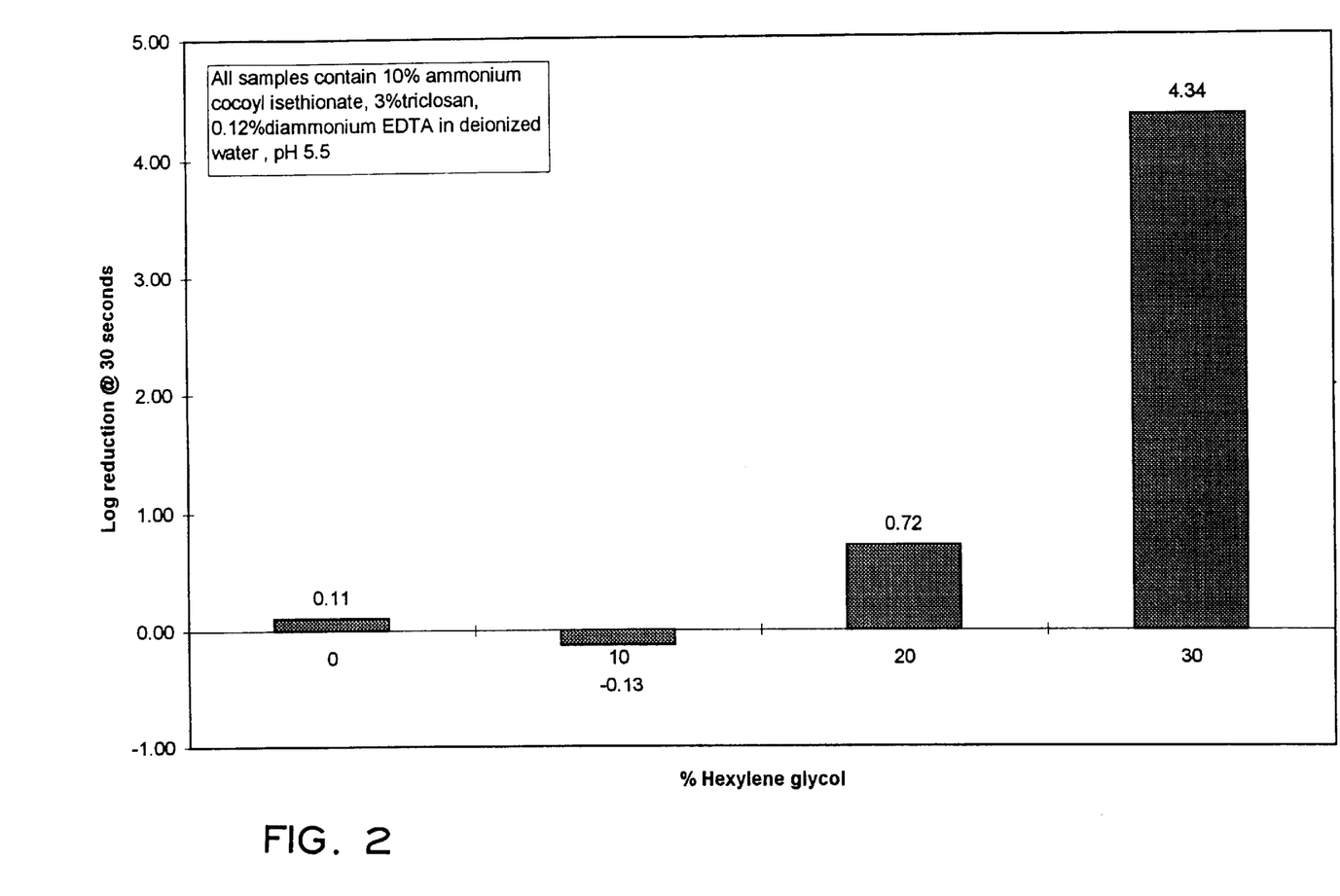
FIG. 2 is a plot of Log reduction of *Serratia marcescens* ATCC 14756 organisms after 30 seconds exposure to 3% triclosan formulations containing 10% ammonium cocoyl isethionate and from 0–30% hexylene glycol.

Several Triclosan skin wash formulations were prepared according to the method described in Example 1. The skin wash formulations contained 3% Triclosan, 10% ammonium cocoyl isethionate, and 0.12% diammonium EDTA in deionized water at pH 5.5. The hand washes were prepared with different concentrations of hexylene glycol, ranging from 0–30%. Log reductions in a population of Serratia marcescens ATCC 14756 were measured after 30 seconds exposure to the hand washes. FIG. 2 shows that the kill rate (log reduction) increased as the hexylene glycol concentration increased. At 30% hexylene glycol, a log reduction of 4.34 was obtained.

Example 5

Figure 3:
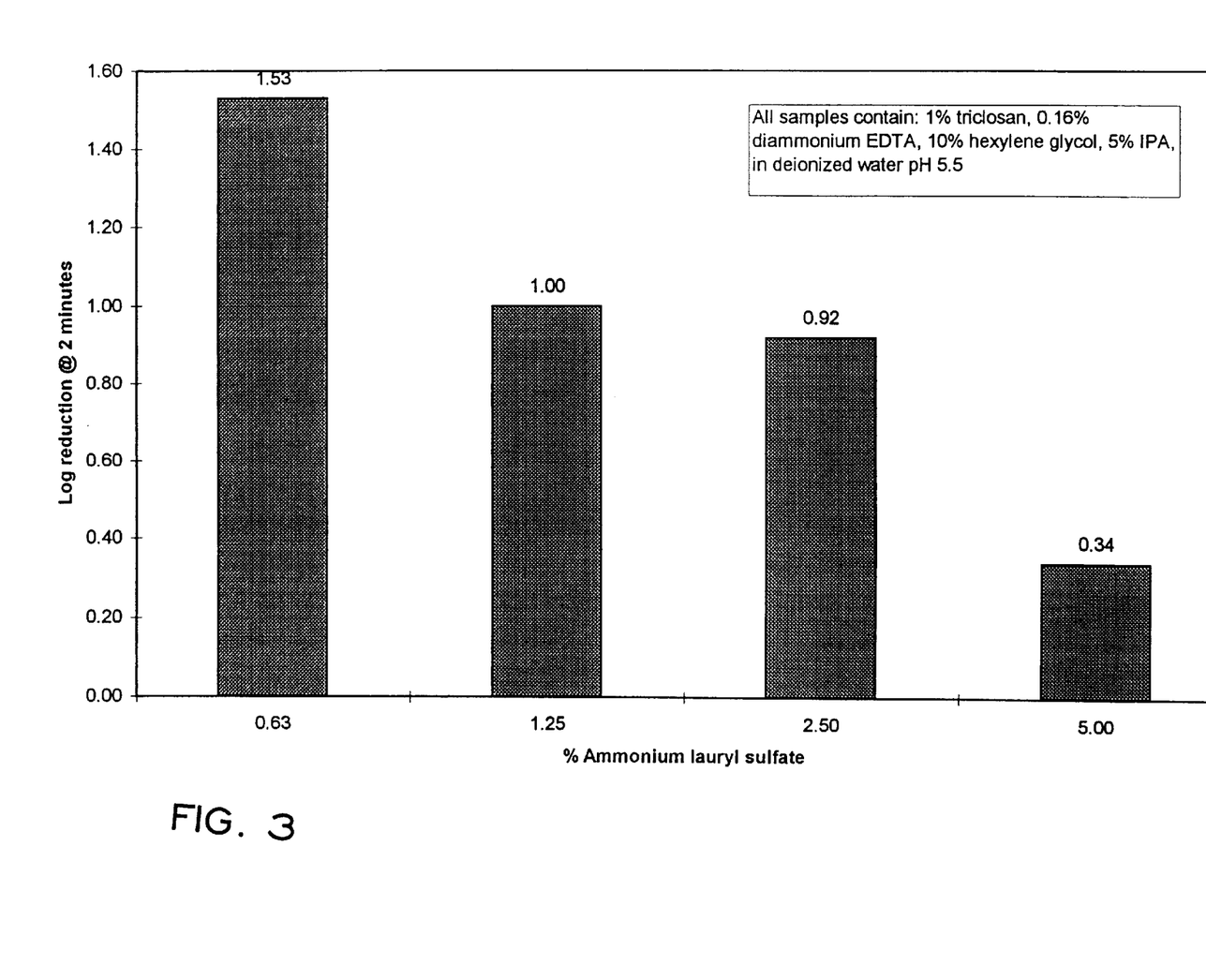
FIG. 3 is a plot of Log reduction of *Serratia marcescens* ATCC 14756 organisms after 2 minutes exposure to 1% triclosan formulations containing 10% hexylene glycol and 0.63–5% ammonium lauryl sulfate.

Effect of Surfactant Concentration on Microorganism Kill for Ammonium Lauryl Sulfate Triclosan skin wash formulations were prepared according to the method described in Example 1. The skin wash formulations contained 1% Triclosan, 10% hexylene glycol, 5% isopropanol, and 0.16% diammonium EDTA in deionized water at pH 5.5. The hand washes were prepared with different concentrations of ammonium lauryl sulfate, ranging from 0.63–5%. Log reductions in a population of Serratia marcescens ATCC 14756 were measured after 2 minutes exposure to the hand washes. FIG. 3 shows that the kill rate (log reduction) increased as the ammonium lauryl sulfate concentration decreased. At 0.63% ammonium lauryl sulfate, a log reduction of 1.53 was obtained, compared with a 0.34 log reduction at 5.0% ammonium lauryl sulfate.

Example 6

Figure 4:
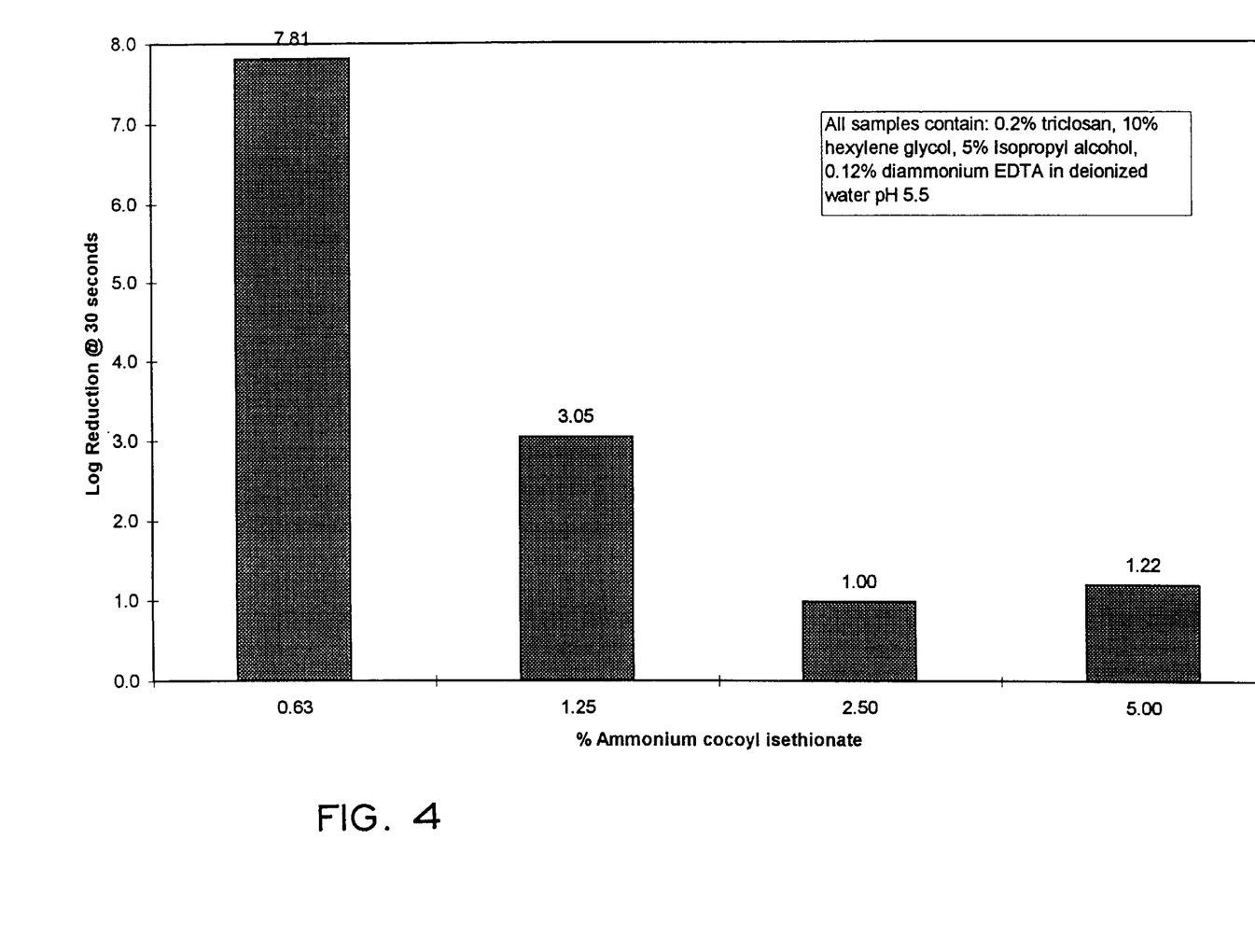
FIG. 4 is a plot of Log reduction of *Staphylococcus aureus* ATCC 6538 organisms after 30 seconds exposure to 0.2% triclosan formulations containing 10% hexylene glycol, 5% isopropanol and 0.63–5% ammonium cocoyl isethionate.

Effect of Surfactant Concentration on Microorganism Kill for Ammonium Cocoyl Isethionate Triclosan skin wash formulations were prepared according to the method described in Example 1. The skin wash formulations contained 0.2% Triclosan, 10% hexylene glycol, 5% isopropanol, and 0.12% diammonium EDTA in deionized water at pH 5.5. The hand washes were prepared with different concentrations of ammonium cocoyl isethionate, ranging from 0.63–5%. Log reductions in a population of Staphylococcus aureus ATCC 6538 were measured after 30 seconds exposure to the handwash. FIG. 4 shows that the kill rate (log reduction) increased as the ammonium cocoyl isethionate concentration decreased. At 0.63% ammonium cocoyl isethionate, a log reduction of 7.81 was obtained, compared with a 1.22 log reduction at 5.0% ammonium cocoyl isethionate.

Example 7

Figure 5:
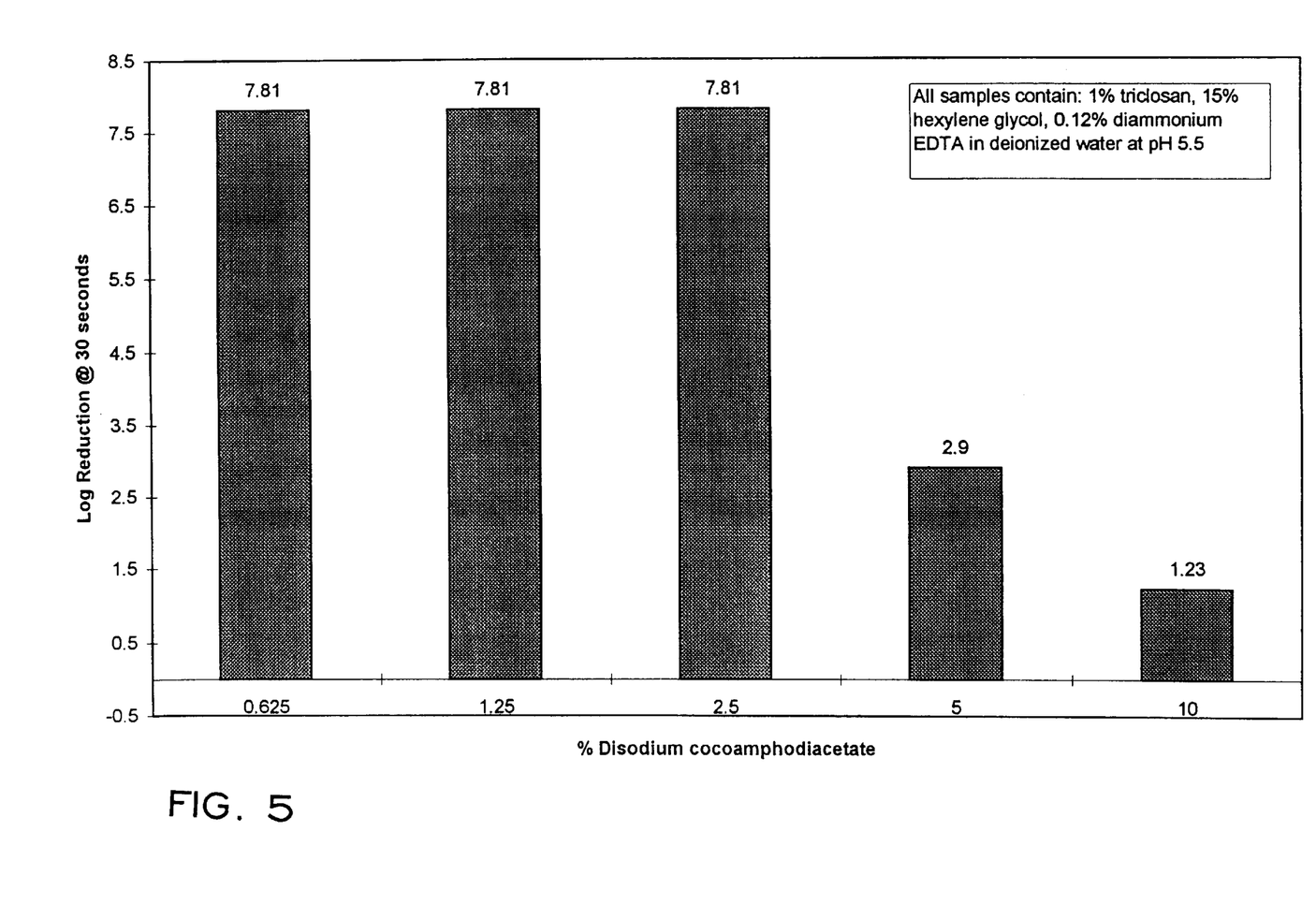
FIG. 5 is a plot of Log reduction of *Staphylococcus aureus* ATCC 6538 organisms after 30 seconds exposure to 1% triclosan formulations containing 15% hexylene glycol and 0.625–10% disodium cocoamphodiacetate.

Effect of Surfactant Concentration on Microorganism Kill for Disodium Cocoamphodiacetate Several Triclosan skin wash formulations were prepared according to the method described in Example 1. The skin wash formulations contained 1% Triclosan, 15% hexylene glycol, and 0.12% diammonium EDTA in deionized water at pH 5.5. The hand washes were prepared with different concentrations of disodium cocoamphodiacetate, ranging from 0.625–10%. Log reductions in a population of Staphylococcus aureus ATCC 6538 was measured after 30 seconds exposure to the handwash. FIG. 5 shows that the kill rate (log reduction) increased as the disodium cocoamphodiacetate concentration decreased. At 0.625–2.5% disodium cocoamphodiacetate, a log reduction of 7.81 was obtained, compared with a 1.23 log reduction at 10.0% disodium cocoamphodiacetate.

Example 8

Figure 6:
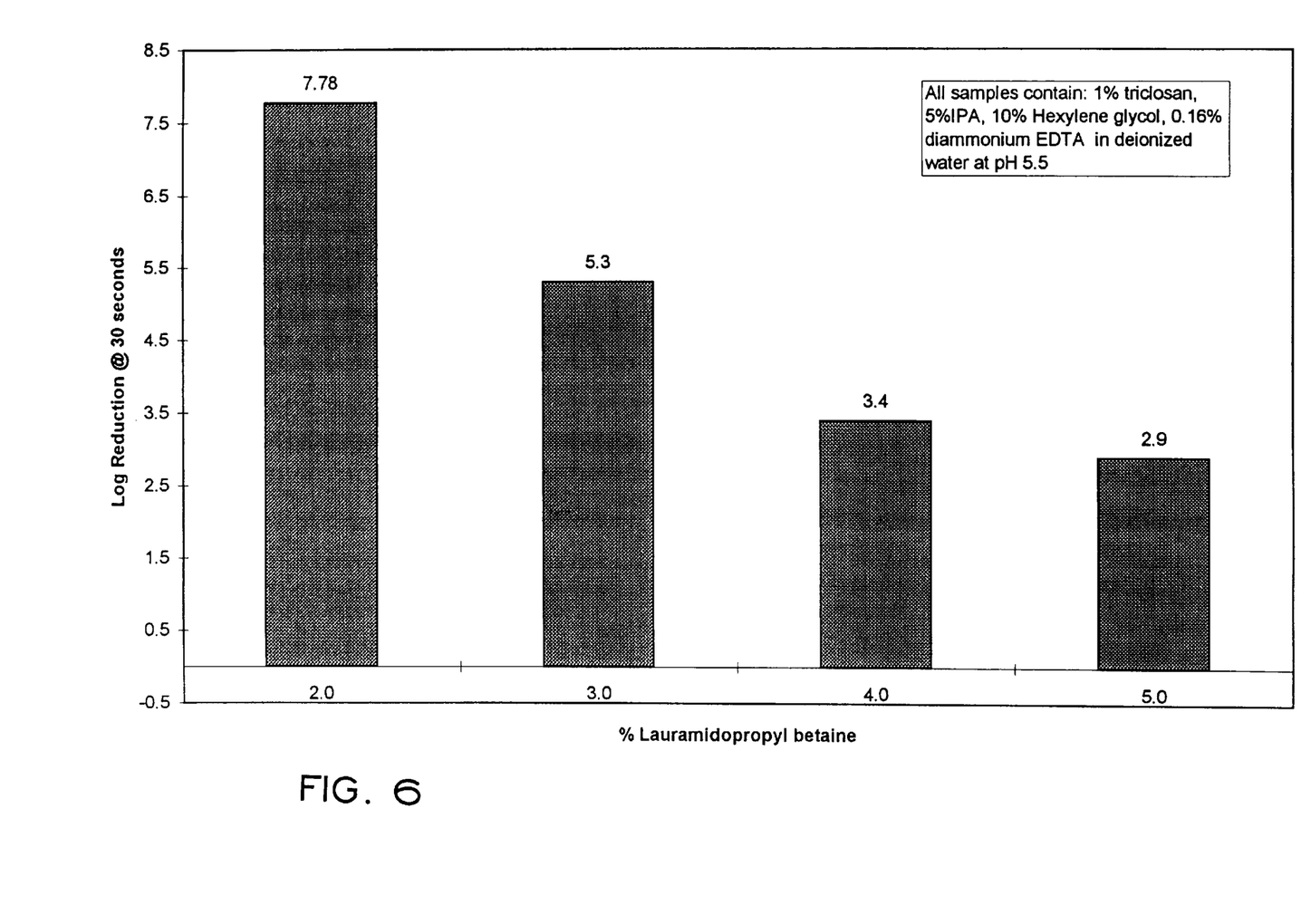
FIG. 6 is a plot of Log reduction of *Staphylococcus aureus* ATCC 6538 organisms after 30 seconds exposure to 1% triclosan formulations containing 10% hexylene glycol, 5% isopropanol and 2–5% ammonium lauramidopropyl betaine.

Effect of Surfactant Concentration on Microorganism Kill for Lauramidopropyl Betaine Several Triclosan skin wash formulations were prepared according to the method described in Example 1. The skin wash formulations contained 1% Triclosan, 10% hexylene glycol, 5% isopropanol, and 0.16% diammonium EDTA in deionized water at pH 5.5. The hand washes were prepared with different concentrations of lauramidopropyl betaine, ranging from 2–5%. Log reductions in a population of Staphylococcus aureus ATCC 6538 were measured after 30 seconds exposure to the handwash. FIG. 6 shows that the kill rate (log reduction) increased as the lauramidopropyl betaine concentration decreased. At 2.0% lauramidopropyl betaine, a log reduction of 7.78 was obtained, compared with a 2.9 log reduction at 5.0% lauramidopropyl betaine.

Example 9

Figure 7:
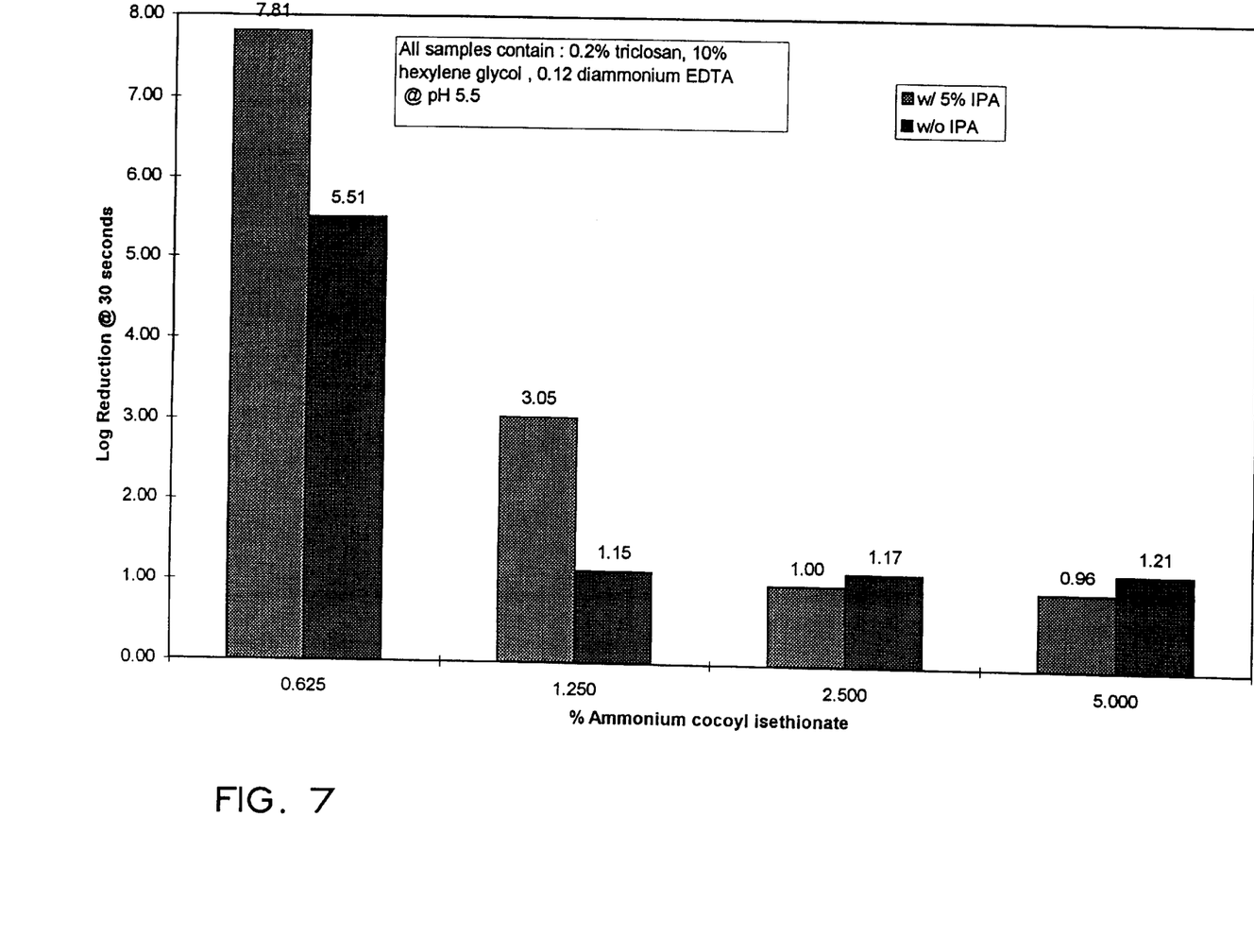
FIG. 7 is a plot of Log reduction of *Staphylococcus aureus* ATCC 6538 organisms after 30 seconds exposure to 0.2% triclosan formulations containing 10% hexylene glycol and 0.625–5% ammonium cocoyl isethionate, both with and without 5% isopropanol.

Effect of Presence of Isopropanol on Microorganism Kill at Different Surfactant Concentrations Several Triclosan skin wash formulations were prepared according to the method described in Example 1. The skin wash formulations contained 0.2% Triclosan, 10% hexylene glycol, and 0.12% diammonium EDTA in deionized water at pH 5.5. The hand washes were prepared with different concentrations of ammonium cocoyl isethionate, ranging from 0.625–5%. Comparison was made with equivalent formulations which also contained 5% isopropanol. Log reductions in a population of Staphylococcus aureus ATCC 6538 were measured after 30 seconds exposure to the handwash. FIG. 7 shows that the kill rate (log reduction) was higher at lower concentrations of surfactant. At below 2.5% surfactant, the log reduction was greater for formulations with isopropanol than those without. For example, at 1.25% surfactant, the kill rate without isopropanol was 1.15 after 30 seconds, whereas, with isopropanol present, the log reduction was 3.05.

Example 10

Effect of Different Co-solvent Formulations on Microorganism Kill

Figure 8:
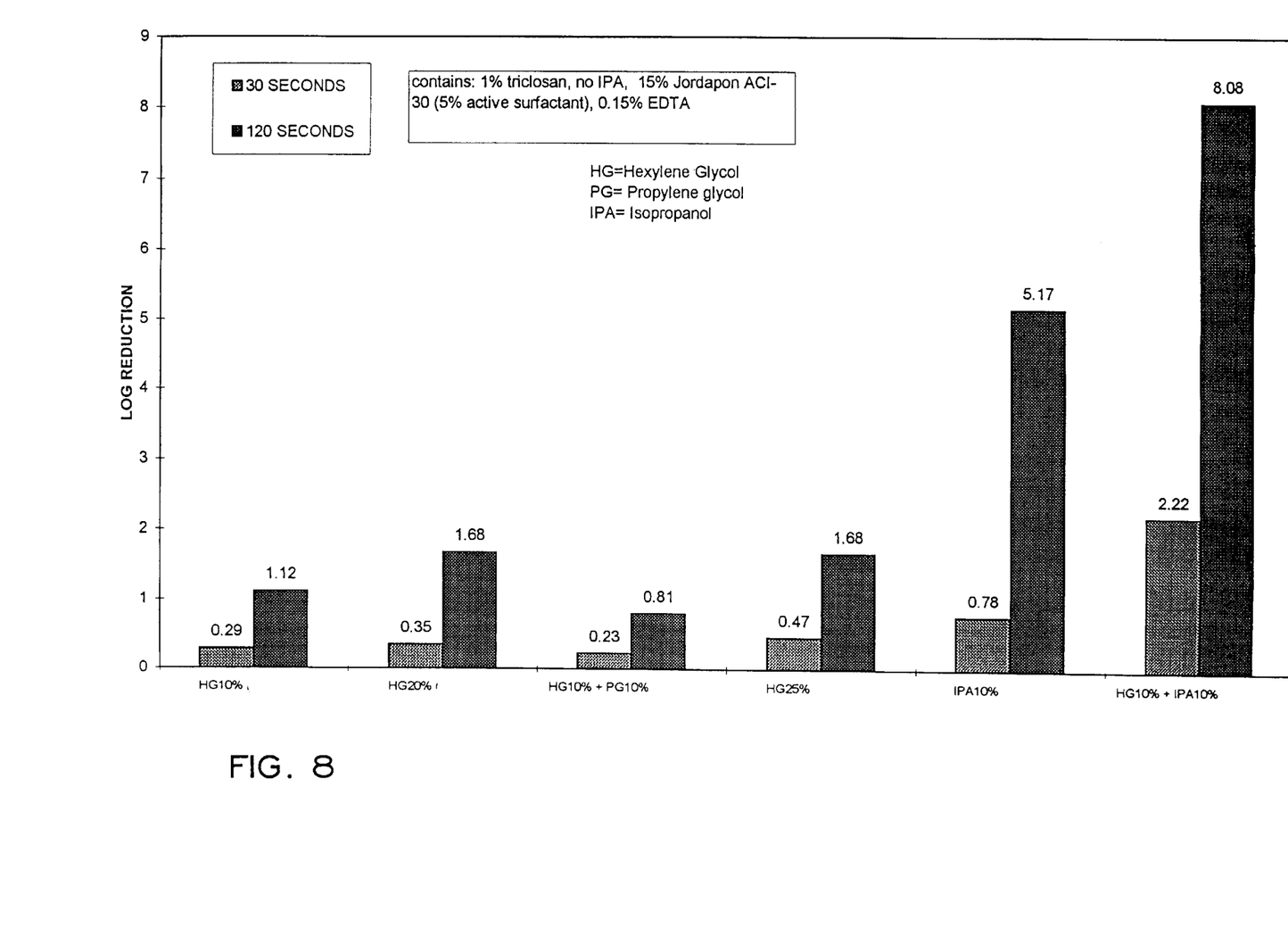
FIG. 8 is a plot of Log reduction of *Serratia marcescens* ATCC 14756 organisms after 30 seconds and 2 minutes exposure to 1% triclosan formulations containing about 5% ammonium cocoyl isethionate and varying amounts of hexylene glycol, propylene glycol, and isopropanol.

Several Triclosan skin wash formulations were prepared according to the method described in Example 1. The skin wash formulations contained 1% Triclosan, 15% Jordapon ACI-30 (i.e., about 4.5% Ammonium Cocoyl Isethionate), and 0.15% diammonium EDTA in deionized water at pH 5.5. The skin washes were prepared with different co-solvent components, namely, hexylene glycol at 10%; hexylene glycol at 20%; hexylene glycol at 25%; hexylene glycol at 10% with propylene glycol at 10%; isopropanol at 10%; and hexylene glycol at 10% with isopropanol at 10%. Log reductions in a population of Serratia ATCC 14756 were measured after 30 seconds exposure to the handwash. FIG. 8 shows that the kill rate (log reduction) was highest with a mixture of 10% hexylene glycol and 10% isopropanol for the 15 triclosan formulation.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A skin wash composition comprising:
    (a) about 0.2 to about 3.0% Triclosan;
    (b) about 1.0 to about 30.0% of a non-aqueous solvent which includes hexylene glycol;
    (c) less than about 10.0% surfactant;
    (d) about 0.0 to about 1.0% chelating agent;
    (e) a thickener present in a sufficient amount to provide a viscosity of at least 500 cps;
    (f) about 0.0 to about 5.0% buffering agent; and
    (g) water.

2. The wash composition of claim 1, wherein the Triclosan concentration is from about 0.3 to about 1.5%.

3. The skin wash composition of claim 1, wherein the non-aqueous solvent is at a concentration of from about 3.0 to about 20.0%.

4. The skin wash composition of claim 1, wherein the non-aqueous solvent further includes a lower alcohol selected from the group consisting of isopropanol, n-propanol, ethanol, and combinations thereof.

5. The skin wash of claim 4, wherein the non-aqueous solvent includes between about 3 and 20% hexylene glycol and about 3–15% of the lower alcohol.

6. The skin wash composition of claim 5, wherein the non aqueous solvent includes:
    10–15% hexylene glycol; and
    5–10% isopropanol.

7. The skin wash composition of claim 1, wherein the surfactant is at a concentration of from about 1.0 to about 5%.

8. The skin wash of claim 1, wherein the surfactant is selected from the group consisting of polyoxyethylene sorbitan fatty acid esters, polyoxyethylene stearates, polyvinyl alcohol, poloxamers, octoxynols, sarcosinates, sulfonates, sulfosuccinates, isethionates, sulfates, amine oxides, taurates, betaines, sultaines, imidazolines, and their derivatives, and combinations thereof.

9. The skin wash of claim 8, wherein the surfactant includes at least one of:
    a) an imidazoline or a derivative thereof selected from the group consisting of amphodiacetates, aminopropionates, alkylaminopropionates, and combinations thereof;
    b) an alkyl ether sulfate of the general formula R-(OCH$_2$CH$_2$)$_n$OSO$_3$—M$^+$, wherein R ranges from C$_8$–C$_{20}$ alkyl and preferably from C$_{12}$–C$_{15}$ alkyl, n is an integer from 1 to 40, preferably from 2–9, and optimally about 3, and M$^+$ is a water soluble cation selected from the group consisting of sodium, potassium, ammonium, and triethanolammonium;
    c) an alkyl sulfate;
    d) an alkyl betaine of the general formula RN$^+$(CH$_3$)$_2$CH$_2$CO$_2$—M$^+$, wherein R ranges from C$_8$–C$_{20}$ alkyl and preferably from C$_{12}$–C$_{15}$ alkyl, and M$^+$ is a water soluble cation selected from the group consisting of sodium, potassium, ammonium, and triethanolammonium;
    e) an amidopropyl betaine of the formula RCONHCH$_2$CH$_2$CH$_2$N$^+$(CH$_3$)$_2$CH$_2$CO$_2$—M$^+$, wherein R ranges from C$_8$–C$_{20}$ alkyl and preferably from C$_{12}$–C$_{15}$ alkyl, and M$^+$ is a water soluble cation selected from the group consisting of sodium, potassium, ammonium, and triethanolammonium;
    f) an amidopropyl sultaine of the formula RCONHCH$_2$CH$_2$N$^+$(CH$_3$)$_2$CH$_2$SO$_3$—M$^+$, wherein R ranges from C$_8$–C$_{20}$ alkyl and preferably from C$_{12}$–C$_{15}$ alkyl, and M$^+$ is a water soluble cation selected from the group consisting of sodium, potassium, ammonium, and triethanolammonium;
    g) an isethionate having the general formula RCOOCH$_2$CH$_2$SO$_3$M, wherein R is alkyl or alkenyl of from about C$_{10}$–C$_{30}$ and M is a water soluble cation selected from the group consisting of sodium, potassium, ammonium, and triethanolammonium;
    h) a sulfosuccinate selected from the group consisting of monoalkyl sulfosuccinates, amido MEA sulfosuccinates, dimethicone copolyol sulfosuccinates; and
    i) a sarcosinate of the general formula RCON(CH$_3$)CH$_2$CO$_2$—M$^+$, wherein R is alkyl from about C$_8$–C$_{20}$, preferably C$_{12}$–C$_{15}$, and M$^+$ is a water soluble cation selected from the group consisting of sodium, potassium, ammonium, and triethanolammonium.

10. The skin wash of claim 9, wherein the surfactant includes ammonium cocoyl isethionate.

11. The skin wash of claim 10, wherein the ammonium cocoyl isethionate is at a concentration of from about 1% to about 5%.

12. The skin wash of claim 1, wherein the chelating agent is at a concentration of from about 0.01 to about 0.5%.

13. The skin wash of claim 1, wherein the thickener is at a concentration of from about 0.50 to about 2.0%.

14. The skin wash of claim 1, wherein the viscosity is between 500 and about 2500 cps.

15. The skin wash of claim 13, wherein the thickener includes one or more of the group including hydroxypropyl methylcellulose, hydroxypropyl cellulose, hydroxyethyl cellulose, guar and guar derivatives, alginate and alginate derivatives, and carbomer.

16. The skin wash of claim 1, wherein the buffering agent buffers the pH of the composition to about pH 5.5.

17. The skin wash of claim 1, wherein the buffering agent includes one or more of the group including acetic acid or acetate salts, citric acid or citrate salts, glycolic acid or glycolate salts, and phosphoric acid or phosphate salts.

18. The wash of claim 17, wherein the buffering agent includes citric acid or citrate salts.

19. A method of disinfecting skin comprising:
  (a) applying to the skin an effective amount of a composition including:
    about 0.2 to about 3.0% Triclosan;
    about 1.0 to about 30.0% of a non-aqueous solvent which includes hexylene glycol;
    less than about 10.0% surfactant;
    about 0.0 to about 1.0% chelating agent;
    a thickener present in a sufficient amount to provide a viscosity of at least 500 cps;
    about 0.0 to about 5.0% buffering agent; and water; and,
  b) maintaining contact between the composition and the skin for sufficient time to kill substantially all microorganisms present on the surface.

20. The method of claim 19, further including adding water and rubbing the surface, thereby removing soil from the surface, followed by rinsing the composition from the skin.

21. A skin wash composition comprising:
  (a) about 0.2 to about 3.0% Triclosan;
  (b) about 1.0 to about 30.0% of a non-aqueous solvent which includes:
    a glycol, and
    a lower alcohol selected from the group consisting of isopropanol, ethanol, and n-propanol;
  (c) less than about 8.0% surfactant;
  (d) about 0.0 to about 1.0% chelating agent;
  (e) a thickener present in a sufficient amount to provide a viscosity of at least 500 cps;
  (f) about 0.0 to about 5.0% buffering agent; and
  (g) water.

22. A skin wash composition comprising:
  (a) 0.2–1.5% Triclosan;
  (b) 2.0–8.0% surfactant;
  (c) 4–15% hexylene glycol;
  (d) 3–10% lower alcohol;
  (e) a buffer which buffers pH to 4.5–6.0; and
  (f) a thickener which adjusts viscosity to 500–2500 cps.

* * * * *